(12) United States Patent
Noro et al.

(10) Patent No.: US 8,704,050 B2
(45) Date of Patent: Apr. 22, 2014

(54) NON-BROWNING APPLE, METHOD FOR PRODUCING THE SAME, AND DRINK AND FOOD USING THE SAME

(75) Inventors: Shouji Noro, Kuroishi (JP); Takashi Sato, Kuroishi (JP); Tomoyuki Kon, Kuroishi (JP); Tomoko Akada, Kuroishi (JP); Tsuyoshi Kudo, Kuroishi (JP); Satoshi Kasai, Kuroishi (JP)

(73) Assignee: Aomori Prefecture, Aomori-shi (JP)

( * ) Notice: Subject to any disclaimer, the term of this patent is extended or adjusted under 35 U.S.C. 154(b) by 470 days.

(21) Appl. No.: 12/279,349

(22) PCT Filed: Mar. 8, 2006

(86) PCT No.: PCT/JP2006/304505
§ 371 (c)(1),
(2), (4) Date: Aug. 14, 2008

(87) PCT Pub. No.: WO2007/102215
PCT Pub. Date: Sep. 13, 2007

(65) Prior Publication Data
US 2009/0019563 A1    Jan. 15, 2009

(51) Int. Cl.
*A01H 5/00*    (2006.01)
*A01H 5/10*    (2006.01)

(52) U.S. Cl.
USPC ....................................................... 800/315

(58) Field of Classification Search
None
See application file for complete search history.

(56) References Cited

U.S. PATENT DOCUMENTS

| PP13,930 P2 * | 7/2003 | Cox |
| PP18,485 P3 * | 2/2008 | Khanizadeh |

FOREIGN PATENT DOCUMENTS

| JP | 62-198372 | 9/1987 |
| JP | 10-136883 | 5/1998 |
| JP | 2000-004781 | 1/2000 |
| JP | 2000-023615 | 1/2000 |
| JP | 2000-139434 | 5/2000 |
| JP | 2002-335859 | 11/2002 |
| JP | 2003-070450 | 3/2003 |

OTHER PUBLICATIONS

Murata et al. 2001. Biosci Biotechnol Biochem 65(2): 383-388.*
Murata et al. J. Agric. Food Chem. 48: 5243-5248, 2000.*
International Search Report for PCT/JP2006/304505, 2 pages, Completed Apr. 6, 2006; Mailed Apr. 18, 2006, by ISA/Japanese Patent Office.

* cited by examiner

*Primary Examiner* — Shubo (Joe) Zhou
*Assistant Examiner* — Keith Robinson
(74) *Attorney, Agent, or Firm* — Fay Sharpe LLP

(57) ABSTRACT

It is intended to provide a method for producing a non-browning apple. Apples in which total polyphenol content is not more than 40 mg/100 g fresh weight in terms of catechin when extracted from apple flesh using methanol and assayed by the Folin-Denis method are used as cross parents and by crossing and breeding them, using a low level of the browning degree of fruit flesh as an index and performing selection based on the index, the non-browning apple is produced. The non-browning apple has a non-browning characteristic that browning of flesh is less likely to occur and a polyphenol oxidase activity is significantly lower than that of a conventional cultivar.

2 Claims, 10 Drawing Sheets

Figure 2-5]
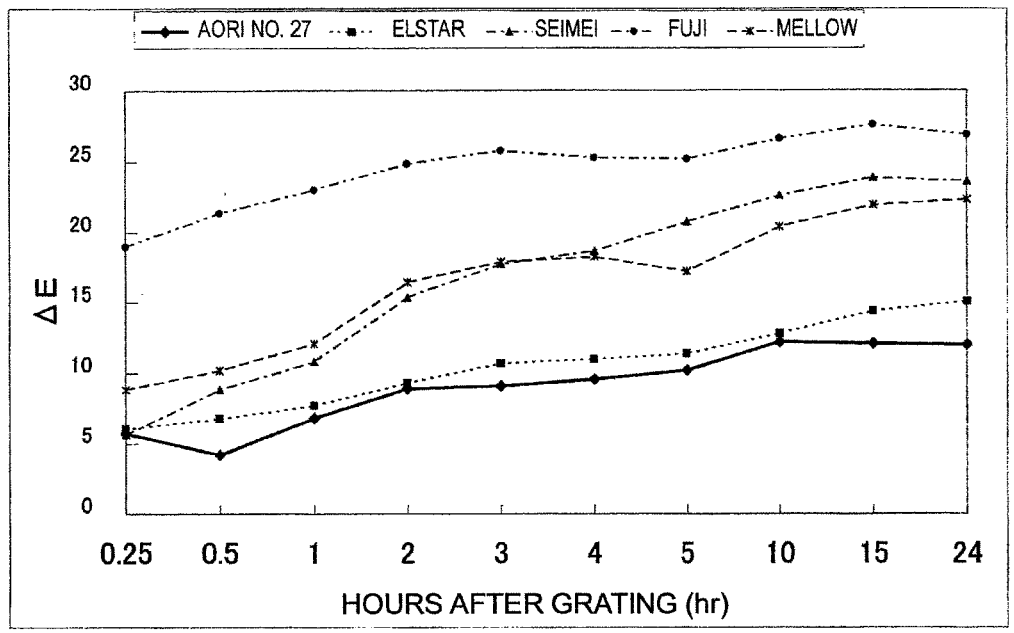
Figure 2-6
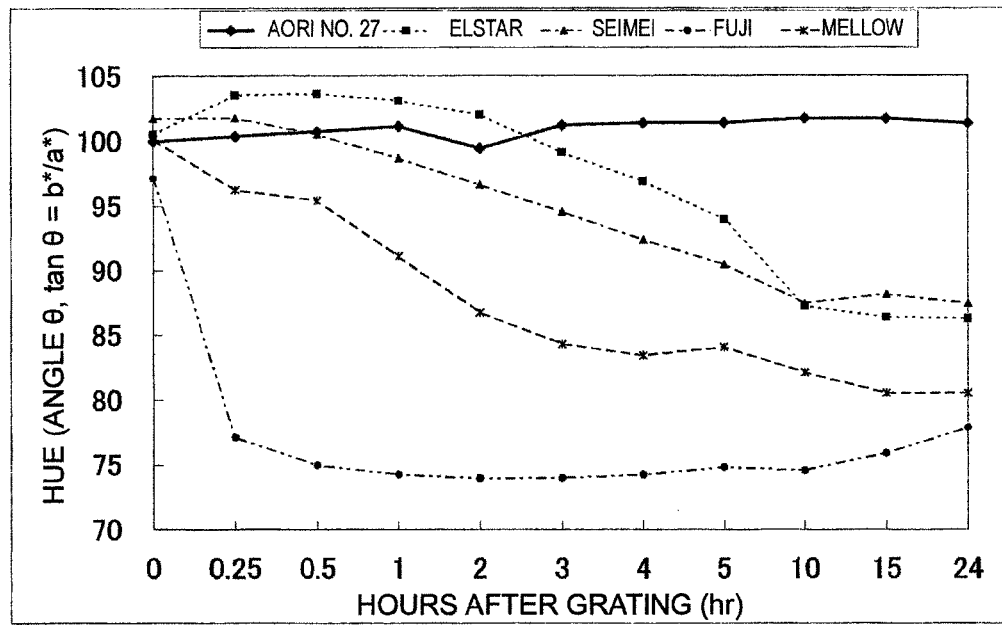

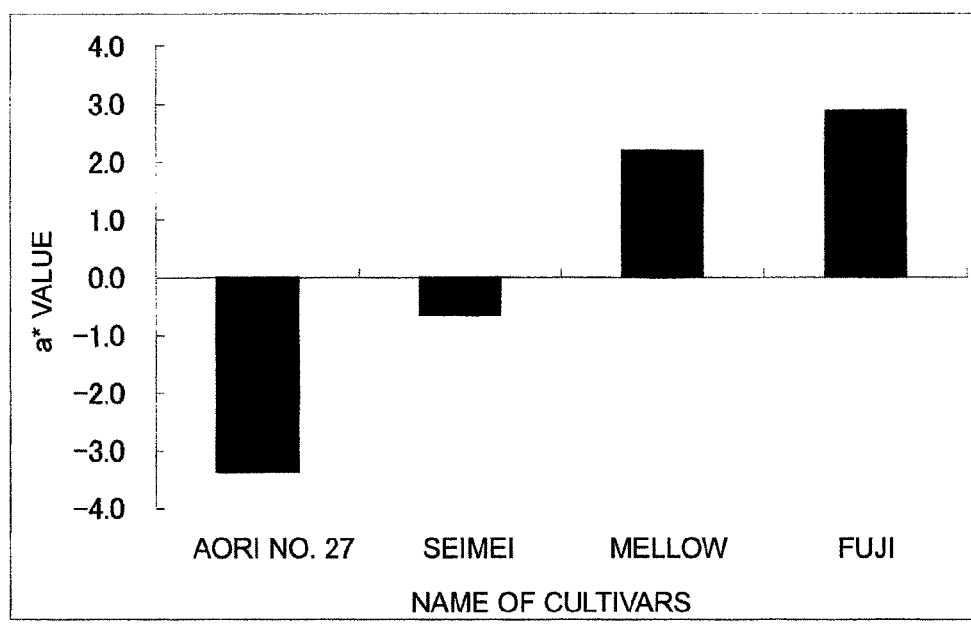
[Figure 4-1]

NON-BROWNING APPLE, METHOD FOR PRODUCING THE SAME, AND DRINK AND FOOD USING THE SAME

TECHNICAL FIELD

The present invention relates to a non-browning apple, a method for producing the same, and drinks and foods using the same, and particularly to a novel non-browning apple having a characteristic that browning does not occur over a long period of time even after grating or the like, a method for producing the same, etc.

BACKGROUND ART

Fruits such as apples turn brown when they are damaged in the process of harvest, shipping and transportation thereof, and mainly due to deterioration of appearances, they may reduce or lose their commercial values. Scratch may also be generated at the time of processing into drinks such as juice or foods or cooking, and in consequence, scratch as well as browning of processed fruits may reduce their commercial values.

In particular, browning is prominent in apples. For example, when grated, cut, or frozen and thawed, browning in apple proceeds at a rapid pace compared to other fruits, and the browning degree thereof is also high. Therefore, the sale in the form of lately-increasing cut fruits or the use in the confectionery industry is consequently very limited.

Accordingly, it can be said that measures against browning in apples are an extremely important challenge for using them to be eaten raw and also for using them in processed foods such as juice or in such commercial forms as cut fruits in order to maintain their commercial value or to increase additional value.

Browning accompanies an enzymatic chemical reaction, which is caused by oxidization of polyphenols contained in plants into quinones by polyphenol oxidase, which finally results in oxidative condensation to a mealanin-like black material. If it is not limited to apples, the following measures against such browning have conventionally be proposed, including addition of an appropriate antioxidant such as ascorbic acid (Japanese Patent Laid-Open No. 10-136883), addition of kojic acid (Japanese Patent Publication No. 5-30422), addition of a fish milt extract (Japanese Patent Laid-Open No. 2000-23615), and addition of an extract of algae such as Chlorococcales (Japanese Patent Laid-Open No. 2000-139434).

Immersion treatments in *Flammulina velutipes* extract (Patent Document 1) and Welsh onion juice with the density of 50 to 100% (Patent Document 2) have also been proposed as measures for those particularly including an apple as an object. In view of preservation, an apple freshness-keeping package has also been disclosed, in which an apple is packed with a synthetic resin film whose oxygen transmittance is 1.5 to 5 cc/24 hr·atm per 1 g of apple so that the oxygen and carbon dioxide concentrations in the bag become 3 to 12% and 8 to 15%, respectively, and the apple respiration rate is suppressed to 30 to 80% in the atmosphere (Patent Document 3).

Patent Document 1: Japanese Patent Laid-Open No. 2003-070450 "Blackening/browning inhibitor for food"
Patent Document 2: Japanese Patent Laid-Open No. 2002-335859 "Method for preventing discoloring of fruits or processed fruits, and anti-discoloring agent for the same"
Patent Document 3: Japanese Patent Laid-Open No. 2000-004781 "Freshness-keeping package for apple"

DISCLOSURE OF THE INVENTION

However, all of these measures against browning are not intended to solve the problem in view of characteristics of apple itself as a plant, but regardless of effectiveness, they have been proposed as measures for avoiding or retarding the generation of browning phenomenon as much as possible at the time of harvesting, shipping and distribution; eating raw; or processing. It means that such measures require special treatments for apple or during apple processing steps. Therefore, there is a natural limit for the effect of browning prevention, reduction in cost and work required therefor, and decrease in commercial and other risks which are caused by addition of foreign matters or the like.

The present invention is directed to providing a non-browning apple and a method for producing the same as a fundamental measure against browning of apple based on the above-described limitation of conventional techniques.

Means for Solving the Problems

The present inventors have studied crossbreeding of apples by using a low level of browning degree of fruit flesh as an index for selection and could obtain an apple in which non-browning characteristic is extremely high according to the present invention. That is to say, the inventions claimed in this application or the inventions at least disclosed herein as means for solving the problems are as follows.

(1) A non-browning apple, characterized by having a non-browning characteristic that browning of flesh is less likely to occur even when the flesh is exposed.

(2) A non-browning apple, characterized by having a non-browning characteristic that browning of flesh is less likely to occur even when the flesh is exposed, wherein the non-browning characteristic meets at least any of the following (A), (B) and (C):

(A) a characteristic that after grated apple flesh prepared by removing the skin and grating the flesh is left at 10 to 25° C. for 1 hour or more, the grated apple flesh does not turn brown;

(B) a characteristic that after flesh prepared by cutting or removing the skin and exposing the flesh is left at 10 to 25° C. for 48 hours or more, the flesh does not turn brown; and (C) a characteristic that after a fruit is frozen and thawed, flesh thereof does not virtually turn brown.

(3) A non-browning apple, characterized by having a non-browning characteristic that browning of flesh is less likely to occur even when the flesh is exposed, wherein the non-browning characteristic ensures that when grated apple flesh prepared by removing the skin and grating the flesh is left at 10 to 25° C. for 1 hour, the following browning index is 0:

browning index: in visual evaluation of browning degree, "non-browning" is designated as 0, "maximum" as 5, and the browning degrees between 0 and 5 are designated as 1, 2, 3, and 4 in phases; and, each index value corresponds to the color chart based on the Japan Color Standard for Horticultural Plants as follows:

browning index 0 2503 (pale yellow), 2504, 2505, 2506 (bright yellow),
1 1913 (yellowish orange),
2 1915 (light yellowish brown),
3 1612 (light brown),
4 1613 (brown) and
5 1608 (bister).

(4) A non-browning apple, characterized by having a non-browning characteristic that browning of flesh is less likely to occur even when the flesh is exposed, wherein the non-browning characteristic ensures that even after grated apple flesh prepared by removing the skin and grating the flesh is left at 10 to 25° C. for 8 hours or more, a color of the grated apple flesh falls into the range of 2503 (pale yellow), 2504, 2505 or 2506 (bright yellow) according to the color chart based on the Japan Color Standard for Horticultural Plants.

(5) A non-browning apple, characterized by having a non-browning characteristic that browning of flesh is less likely to occur even when the flesh is exposed, wherein the non-browning characteristic ensures that when grated apple flesh prepared by removing the skin and grating the flesh is left at 10 to 25° C. for 5 hours, the results of measurement with a color/color difference meter meet at least one of the following (5a) to (5c):

(5a) an a* value after the lapse of 5 hours is not more than −3.00;

(5b) change between an a* value immediately after grating (within 1 minute after grating) and an a'* value after the lapse of 5 hours, i.e., a Δa* value (a'*−a*), is not more than 1.00; and (5c) hue (angle: θ, tan θ=b*/a*) after the lapse of 5 hours is not less than 100.

(6) A non-browning apple, characterized by having a non-browning characteristic that browning of flesh is less likely to occur even when the flesh is exposed, wherein the non-browning characteristic ensures that when grated apple flesh prepared by removing the skin and grating the flesh is left at 10 to 25° C. for 24 hours, the results of measurement with a color/color difference meter meet at least one of the following (6a) to (6c):

(6a) an a* value after the lapse of 24 hours is not more than −2.00;

(6b) change between an a* value immediately after grating (within 1 minute after grating) and an a'* value after the lapse of 5 hours, i.e., a Δa* value (a'*−a*), is not more than 1.00; and (6c) hue (angle: θ, tan θ=b*/a*) after the lapse of 24 hours is not less than 100.

(7) A non-browning apple, characterized by having a non-browning characteristic that browning of flesh is less likely to our even en the flesh is exposed, wherein the non-browning characteristic ensures that when grated apple flesh prepared by removing the skin and grating the flesh is left at 10 to 25° C. for 3 days, the results of measurement with a color/color difference meter meet at least one of the following (7a) and (7b):

(7a) an a* value after the lapse of 3 days is not more than −1.00; and (7b) hue (angle: θ, tan θ=b*/a*) after the lapse of 3 days is not less than 90.0.

(8) A non-browning apple, characterized by having a non-browning characteristic that browning of flesh is less likely to occur even when the flesh is exposed, wherein the non-browning characteristic ensures that when an apple is frozen at −15° C. or less and left at 10 to 25° C. for 1 day after taking out of a freezer, a color of the apple flesh falls into the range of 2503 (pale yellow), 2504, 2505 or 2506 (bright yellow) according to the color chart based on the Japan Color Standard for Horticultural Plants, which means that the browning index according to claim 3 is 0.

(9) A non-browning apple, characterized by having a non-browning characteristic that browning of flesh is less likely to occur even when the flesh is exposed, wherein the non-browning characteristic ensures that when an apple is frozen at −15° C. or less, and left at 10 to 25° C. for 1 day after taking out of a freezer, the results of measurement with a color/color difference meter meet at least one of the following (9a) and (9b):

(9a) an a* value in 1 day after taking out of a freezer is not more than −3.00; and (9b) hue (angle: θ, tan θ=b*/a*) in 1 day after taking out of a freezer is not less than 96.0.

(10) The non-browning apple as defined in any of (1) to (9), characterized in that the polyphenol oxidase activity is not more than 100 units/100 g per fresh weight when measured for apple flesh by a calorimetric method using chlorogenic acid as a substrate in accordance with a method reported by (M) Murata et al. (Journal of the Japanese Society for Food and Science Technology, 1995).

(11) The non-browning apple as defined in any of (1) to (9), characterized in that the polyphenol oxidase activity is not less than 50 units/100 g and not more than 70 units/100 g per fresh weight when measured for apple flesh by a colorimetric method using chlorogenic acid as a substrate in accordance with a method reported by (M) Murata et al. (Journal of the Japanese Society for Food and Science Technology, 1995).

(12) The non-browning apple as defined in (10) or (11), characterized in that a total polyphenol content is not more than 40 mg/100 g per fresh weight in terms of catechin when polyphenol is extracted from apple flesh using methanol and measured by the Folin-Denis method.

(13) The non-browning apple as defined in any of (1) to (12), characterized by having every characteristic of the following (13a) to (13c):

(13a) having an incompatible genotype of s7s9;

(13b) being mutually cross compatible with cultivars "Fuji", "Tsugaru" and "Ourin"; and (13c) being compatible as a pollenizer of cultivar "Jonagold".

(14) The non-browning apple as defined in (13), characterized by having every characteristic of the following (14a) to (14d):

(14a) having maturity about 1 day earlier than "Ourin";

(14b) having a tree attitude of intermediate and tree size and vigor of both medium, with frequent generation of burr knot;

(14c) having high productivity due to easy flow-bud formation and spur bearing; and (14d) having strong resistance to *Alternaria* blotch.

(15) The non-browning apple as defined in (1) to (14), characterized by having a non-browning characteristic that browning of flesh is less likely to occur, wherein the non-browning apple is produced by crossing apples with a characteristic of low total polyphenol content as cross parents; breeding hybrids thereof; and using a low level of browning degree of flesh as an index to perform selection.

(16) The non-browning apple as defined in (15), characterized in that one of apples used as the above-described cross parents is cultivar "Kinsei", while the other one is cultivar "Mahe 7" derived from crossing between cultivar "No. 5" and cultivar "Redgold", which "No. 5" is derived from crossing between cultivar "Indo" and cultivar "Golden Delicious".

(17) A method for producing a non-browning apple, characterized by obtaining an apple having a non-browning characteristic that browning of flesh is less likely to occur, wherein the non-browning apple is produced by crossing apples with a characteristic of low total polyphenol content; breeding hybrids thereof; and using a low level of browning degree of flesh as an index to perform selection.

(18) The method for producing a non-browning apple as defined in (17), characterized in that one of apples used as the cross parents is cultivar "Kinsei", while the other one is cultivar "Mahe 7" derived from crossing between cultivar "No. 5" and cultivar "Redgold", which "No. 5" is derived from crossing between cultivar "Indo" and cultivar "Golden Delicious".

(19) A method for producing a non-browning apple, characterized by obtaining an apple having a non-browning characteristic that browning of flesh is less likely to occur, wherein the non-browning apple is produced by crossing apples with a total polyphenol content of not more than 40 mg/100 g per fresh weight in terms of catechin when the polyphenol is extracted from apple flesh using methanol and measured by the Folin-Denis method as cross parents; breeding hybrids thereof; and using a low level of browning degree of flesh as an index to perform selection.

(20) Non-browning drinks or foods manufactured by using the non-browning apple as defined in any of (1) to (19).

The non-browning apple of the present invention has been produced by cross breeding based on certain selection conditions as described above. Upon filing the present application, this apple has applied for registry of cultivar as "Aori No. 27" according to the seed and seedling law. The inventive non-browning apple may be referred to as cultivar "Aori No. 27" or just "Aori No. 27" in the following description.

As described above, the non-browning apple according to the present invention is completely different from conventional apples and has a characteristic that the apple itself as a plant does not turn brown, or browning proceeds at extremely slow pace and the degree thereof is very low. That is to say, a "non-browning" characteristic according to the present invention can be defined as virtually "unbrowning". Therefore, in accordance with the present invention primarily for such a non-browning apple, since it is possible to provide virtually "unbrowning" of apples at various scenes including harvest, shipping and distribution; eating raw; processing; or taking a commercial form such as cut fruits, the non-browning apple has great advantages for improving and maintaining its commercial value. It is also possible to expand apple processing applications and increase consumption.

In addition, according to the present invention, it is needless to say that measures for browning prevention, which are conventionally required, can be eliminated fundamentally. That is to say, special treatments, which are conventionally required for apple or in apple processing steps, become absolutely unnecessary, thereby avoiding costs and works necessary for such special treatments as well as commercial and other risks caused by addition of foreign matters or the like.

Further, it is also possible to develop new products such as processed foods utilizing the "unbrowning" characteristic. For example, is considered that cut vegetables or cut fruits can be treated as merchandise if they are in the unbrowning state for about 2 days after processing. A non-browning apple of the present invention satisfies such a condition without any difficulty. In addition, since browning does not occur over several days after grating, and also after freezing and thawing, it is thought to develop new products such as sol-form foods or frozen foods.

BRIEF DESCRIPTION OF THE DRAWINGS

FIG. 2-1 is a graph showing change over time up to 24 hours in L* values of grated apples;

FIG. 2-2 is a graph showing change over time up to 24 hours in a* values of grated apples;

FIG. 2-3 is a graph showing change over time up to 24 hours in b* values of grated apples;

FIG. 2-4 is a graph showing change over time up to 24 hours in E* values of grated apples;

FIG. 2-5 is a graph showing change over time up to 24 hours in ΔE values of grated apples;

FIG. 2-6 is a graph showing change over time up to 24 hours in hue of grated apples;

FIG. 3-1 is a graph showing change over time up to 5 days later in L* values of grated apples;

FIG. 3-2 is a graph showing change over time up to 5 days later in a* values of grated apples;

FIG. 3-3 is a graph showing change over time up to 5 days later in b* values of grated apples;

FIG. 3-4 is a graph showing change over time up to 5 days later in color difference ΔE values of grated apples;

FIG. 3-5 is a graph showing change over time up to 5 days later in hue (angle: θ, tan θ=b*/a*) of grated apples;

FIG. 4-1 is a graph showing the results of measurement for a* values of apples in 1 day after taking out of a freezer;

FIG. 4-2 is a graph showing hue (angle: θ, tan θ=b*/a*) in 1 day after taking out of a freezer.

BEST MODE FOR CARRYING OUT THE INVENTION

The present invention will now be described in detail with reference to the actual process of producing a non-browning apple, general characteristics of the apply and the test results of non-browning characteristic of the apple, and the like.

<1. Process of Production>

A process of producing a non-browning apple "Aori No. 27" is as follows.

1) Crossing (1983): It was conducted in the combination of Kinsei and Mahe 7. It is to be noted that Mahe 7 is derived from crossing between No. 5 (Indo and Golden Delicious) and Redgold. The crossing was performed in the process of a test for breeding new apple cultivars, which test was commenced on 1970 at the Aomori Prefectural Apple Experiment Station.

2) First selection (1997): It was found in 1999 that the inventive apple did not turn brown in a physical and chemical analysis of nurtured fruits. Then, when flesh was grated and left over night, color change thereof was that the yellow color became slightly deeper than that immediately after grating, but browning did not occur. Therefore, the index set for selection is that browning does not occur even when flesh is grated or cut and exposed.

3) Second selection (2004)

4) Local adaptability test (April 2005)

Cultivar was first named "Aori (kanji) No. 27", and then "Aori (hiragana) No. 27".

<2. Fruit Characteristics>

The main fruit characteristics of "Aori No. 27" are as follows.

1) Season of maturity: Middle or late October.

2) Size: About 300 g.

3) Skin color: Sanguine, indistinct stripes, and conspicuous fruit spot rust.

4) Shape: Conical to round, and fruit shape uniformity is middle.

5) Flesh quality: 17 to 18 pounds in firmness, and coarse in texture.

6) Eating quality: Percentage of sugar content is about 15% (13 to 15% for cultivar "Fuji"), and acid level is about 0.25 g/100 ml (0.4 g/100 ml for "Fuji"). It is aromatic, less acidic and sweet.

7) Keeping quality: Can be kept up to about 2 months at general refrigerating in the case of eating raw.

Figure 1P:
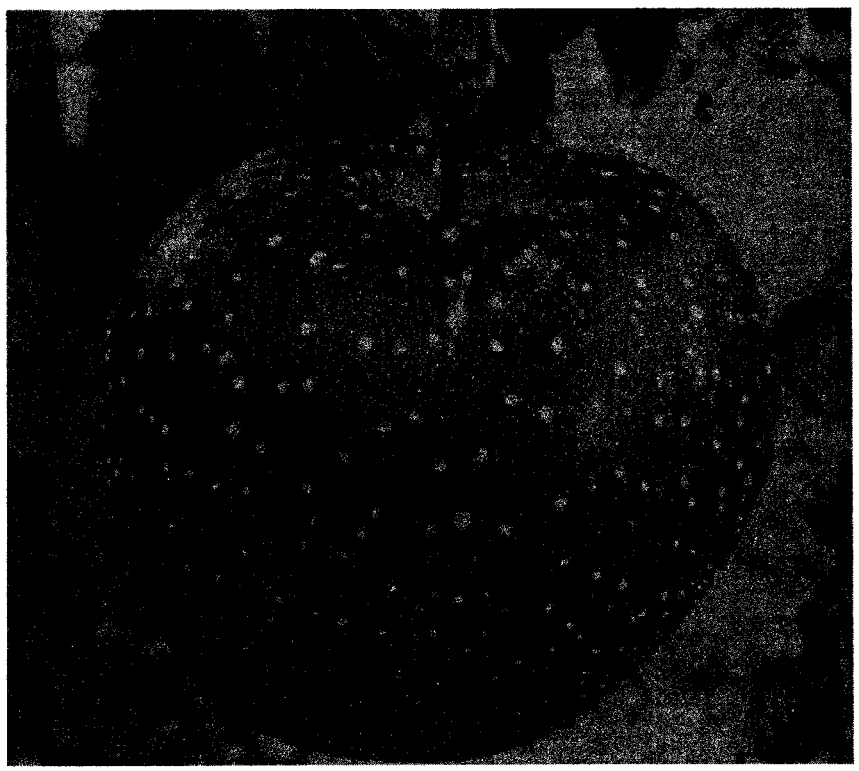
FIG. 1P is a photograph of a fruit of "Aori No. 27", a non-browning apple of the present invention.

Just for reference, a photograph of a fruit of "Aori No. 27", a non-browning apple of the present invention, is shown in FIG. 1P.

It also has the following characteristics.

Browning of flesh is less likely to occur.

(As described hereinafter), it hardly turns brown even when grated flesh is left for about 1 week.

No honey.

Conspicuous fruit spot rust.

Core rust is frequently generated, but it is just to make locules blackened.

<3. Characteristics of Plant, Points of Concern when Cultivating>

"Aori No. 27" has the following characteristics of plant.

1) having maturity about 1 day earlier than "Ourin".

2) having a tree attitude of intermediate and tree size and vigor of both medium, with frequent generation of burr knot.

3) having high productivity due to easy flow-bud formation and spur bearing.

4) having strong resistance to Alternaria blotch.

5) having an incompatible genotype of "Aori No. 27" of s7s9, and being mutually cross compatible with cultivars "Fuji", "Tsugaru" and "Ourin". In addition, also being compatible as a pollenizer of cultivar "Jonagold".

Moreover, when harvesting, it should be concerned to avoid overripe of fruits and keep the amount of bearing the appropriate level.

<4. Polyphenol Oxidase Activity>

It is thought that the difference of enzymatic browning among cultivars depends on the content of polyphenols and the activity of polyphenol oxidase, an enzyme that oxidizes polyphenols. Accordingly, in order to clarify a mechanism that flesh of "Aori No 27" does not turn brown, a polyphenol oxidase activity (hereinafter also called "PPO activity") was measured and compared with those of other several cultivars.

1) Cultivars Under Test

Table 1 shows test cultivars.

TABLE 1

| Cultivars in which browning is less likely to occur | Cultivars in which browning easily occurs | Parent cultivars of Aori No. 27 |
|---|---|---|
| Aori No. 27, Mellow, Elstar, Seimei, Hida, Akita gold | Ourin, Fuji (control) | Kinsei, Mahe 7 |

2) Preparation of Acetone Powders

To 10 g of flesh with the skin and core removed therefrom was added 30 ml of 100% cold acetone. The mixture was crushed in a blender (4° C., 15,000 rpm, 1 min) and then centrifuged (4° C., 5,000 rpm, 5 min) to obtain a precipitate. The resulting precipitate was washed with 20 ml of 80% cold acetone. Thereafter, the wash was repeated twice, followed by centrifugation (4° C., 5,000 rpm, 5 min). The precipitate thus obtained was dried under reduced pressure to obtain acetone powder and its weight was measured.

3) Preparation of Crude Enzyme Liquid

To 0.5 g of acetone powder was added 40 ml of McIlvaine buffer (pH 5.0). After the mixture was crushed with homogenizer (4° C., 12,000 rpm, 5 min), a filtrate obtained by suction filtration was centrifuged (4° C., 9,000 rpm, 30 min) to obtain a supernatant thereof as a crude enzyme liquid.

4) Measurement of Polyphenol Oxidase Activity

Chlorogenic acid was used as a substrate, while the composition of the reaction solution was 1.6 ml of crude enzyme liquid, 0.4 ml of 1 mM solution of chlorogenic acid and 2.0 ml of distilled water. The reaction was conducted under the condition of 300° C. and the absorbance (325 nm) was measured. The activity was taken as 1 unit, when the absorbance was reduced by 0.01 per 1 min.

4) Measurement Results

Figure 1:
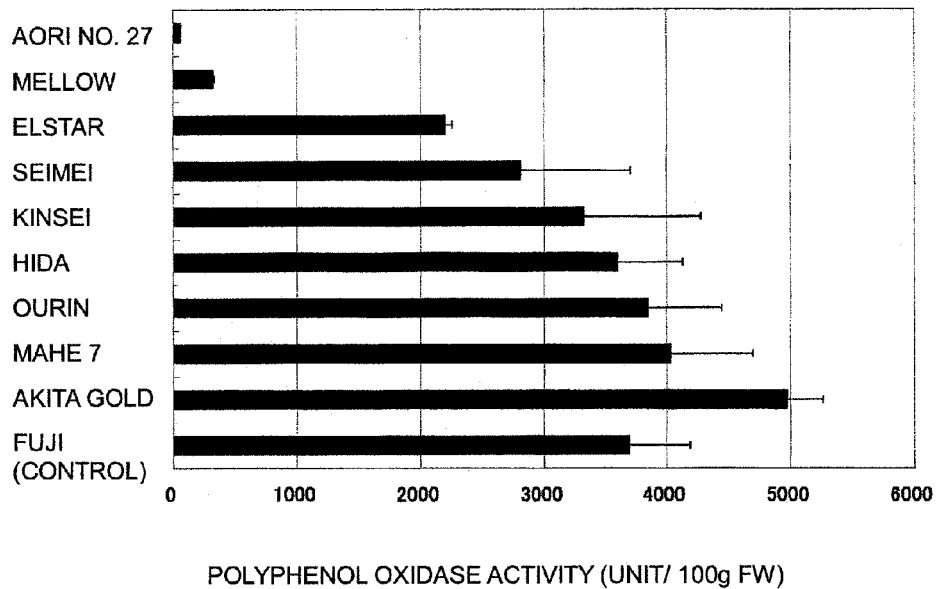
FIG. 1 is a graph showing the results of measurement for polyphenol oxidase activity of each apple cultivar including "Aori No. 27" of the present invention.

The results of measurement for polyphenol oxidase activity of each apple cultivar including "Aori No. 27" of the present invention are shown in Table 2. Further, FIG. 1 is a graph showing the results of measurement for polyphenol oxidase activity of each apple cultivar including "Aori No. 27". As shown by these results, the flesh polyphenol oxidase activities of "Aori No. 27" and "Mellow" were lower than those of other cultivars. In particular, such an activity was extremely low for "Aori No. 27" (62 units), which was about one-sixtieth of "Fuji" (3689 units), a control. Regardless of how easily browning occurs, other cultivars showed the same level of activity as "Fuji". Further, the activities of both "Kinsei" and "Mahe 7", which are parents of "Aori No. 27", were at the same level as "Fuji". As described above, the flesh polyphenol oxidase activity of "Aori No. 27" of the present invention was extremely low, which was one-sixtieth of "Fuji". This was believed to be one of main factors that browning of flesh does not occur over a long period of time.

TABLE 2

Polyphenol oxidase activity (unit/100 g FW)

|  | Fuji (control) | Akita gold | Mahe 7 | Ourin | Hida | Kinsei | Seimei | Elstar | Mellow | Aori No. 27 |
|---|---|---|---|---|---|---|---|---|---|---|
| Average | 3689 | 4969 | 4032 | 3848 | 3597 | 3322 | 2804 | 2199 | 326 | 62 |
| Standard deviation | 295 | 499 | 289 | 669 | 598 | 536 | 957 | 899 | 59 | 6 |

<5. Total Polyphenol Content>
1) Cultivars Under Test
"Aori No. 27" and other 9 cultivars were under test (refer to Table 3 hereinafter indicated).
2) Extracts of Polyphenol
To 10 g of flesh was added 30 ml of 100% methanol. The mixture boiled under reflux for 10 minutes and then ground in a mortar, followed by filtration through gauze. To the residue was added 20 ml of 80% methanol. After shaking for 10 minutes, the mixture was again ground in a mortar and filtered through gauze. The residue was subjected to another shaking and extraction, followed by filtration. The resulting filtrate was quantitated to 100 ml. Repetition was limited to three per cultivar and strain.
3) A total polyphenol content was measured by the Folin-Denis method. The calibration curve was generated by using (+)-catechin (SIGMA) as a standard.
4) Measurement Results
The results of measurement for a total polyphenol content are shown in Table 3 hereinafter indicated. As shown in the table, there was a great difference in total polyphenol content of 10 investigated cultivars depending on cultivars. The total polyphenol content of "Hida" was 16.8 mg/100 gfw, which was the lowest of all. Meanwhile, the total polyphenol content of "Mellow" was 86.0 mg/100 gfw, which was the highest of all. "Aori No. 27" and its parents, "Kinsei" and "Mahe 7" also had low total polyphenol contents, which were 20.0 mg/100 gfw for "Aori No. 27", and 28.8 mg/100 gfw and 23.5 mg/100 gfw for "Kinsei" and "Mahe", respectively.

The results of measurement for both PPO activity and total polyphenol content revealed that flesh of "Aori No. 27" is less likely to turn brown due to low content of "total polyphenol" serving as a substrate of browning, as well as significantly low PPO activity.

<6. Comparison of Browning Degree in Grated Apples (No. 1) Browning Degree 1 Day After Grating>
1) Cultivars Under Test
As well as <5>, 10 cultivars including "Aori No. 27" of the present invention were under test (refer to Table 3).
2) Investigation of Browning Degree Based on Browning Index
A fruit of each cultivar under test was used. Flesh prepared by removing the skin and grating the flesh was put on a foam tray to investigate the browning degree in 1 day after grating. In this investigation, a phrase "immediately after grating" means within 1 minute after grating. It has the same meaning also in the following investigations and measurements. Grating was performed by using a plastic grater. After removing the skin of a fruit (weight: 250 to 350 g), grating was conducted at room temperature (10 to 25° C.) for 20 to 30 seconds of treatment time.

The browning degree was indicated in 6 stages, i.e., no browning in 0 and the darkest browning color in 5. The browning colors of index 0 to 5 correspond to the color chart based on the Japan Color Standard for Horticultural Plants as follows: index 0 to 2503 (pale yellow), 2504, 2505 or 2506 (bright yellow); index 1 to 1913 (yellowish orange); index 2 to 1915 (light yellowish brown); index 3 to 1612 (light brown); index 4 to 1613 (brown); and index 5 to 1608 (bister).

3) Measurement with Color/Color Difference Meter
The color difference immediately after grating and in 1 day after grating was measured for the grated flesh under test indicated in 2) with using a color/color difference meter (CR-300, produced by Minolta). The grated flesh was clothed in Saran Wrap, and then a measurement head was put thereon for measurement. Three parts per cultivar were measured to figure out the average.

4) Findings of Browning Index
Table 3 is a summary table showing the results of measurement for comparison of browning degree in grated apples (No. 1). As shown in the table, the browning indexes of most of investigated cultivars were not less than 3. Cultivars of the browning index 2 that browning is less likely to occur included "Seimei", "Elstar", "Rubens" and "T95". The browning index of "Aori No. 27" was 0, so browning never occurred, but the yellow color became somewhat darker. In the case of the browning index 2, browning is relatively less likely to occur, but in view of the "light yellowish brown" color, the browning phenomenon apparently occurs. In addition, there was no cultivar whose browning index was 1. Accordingly, the "unbrowning" characteristic of "Aori No. 27" whose browning index was 0 was far ahead of others. For reference, the findings of browning index of further more cultivars are shown in Table 4.

TABLE 3

Total polyphenol content, browning index, value of color/color difference meter and PPO activity of apple cultivars

| Name of cultivars | Total polyphenol content (mg/100 gfw) | Browning index (1 day after grating) | Color difference ΔE | PRO activity unit/ 100 gfw | Remarks |
| --- | --- | --- | --- | --- | --- |
| Aori No. 27 | 20.0 | 0.0 | 12.6 | 62 | |
| Hida | 16.8 | 2.0 | 18.9 | 3597 | |
| Seimei | 39.4 | 2.0 | 18.9 | 2804 | |
| Elstar | 48.6 | 2.0 | 20.1 | 2199 | |
| Akita gold | 41.6 | 3.0 | 24.3 | 4969 | |
| Mellow | 86.0 | 3.0 | 27.9 | 326 | |
| Mahe 7 | 23.5 | 5.0 | 24.3 | 4032 | Pollen parent of Aori No. 27 |
| Kinsei | 28.8 | 5.0 | 28.6 | 3322 | Seed parent of Aori No. 27 |
| Ourin | 59.1 | 5.0 | 25.6 | 3848 | |
| Fuji | 52.7 | 5.0 | 30.1 | 3689 | |

TABLE 4

Difference of browning degree among cultivars

| Browning index | Name of cultivars |
| --- | --- |
| 0 | Aori No. 27 |
| 1 | |
| 2 | Hida, Seimei, T95, Rubens, Elstar |
| 3 | Senshu, Shinano Gold, Tsugaru, Aori No. 16, Toko, Redgold, Kanki, Golden Delicious, Mellow, Akita gold, Coatland, Empire |
| 4 | Indo, Granny Smith, Shizuka, Sekaiichi, Narihokou, Freedom, Priam, Toki, Rom 50, Kitakurenai, Kai 5, Mutsu, Trent, Breban, Ourei, Chinatu, Himekami, Fukunishiki, Jonagold, Kougyoku, 155-47, Shinano Sweet, Sayaka, Hatsu Shiga, Akagi |
| 5 | Koko, Slim Red, Fuji, 200-27, Akane, Santaro, Akibae, Koutaro, Starking Delicious, Rome Beauty, Aori No. 12, Kinsei, Ambitious, Yukari, Ourin, Natsumidori, Saika, 4-no-23, Hoozuri, Gunmameigetsu, Hokuto, Gala, Aika-no-Kaori, Asahi, Hoshi-no-Kinka, Northern Spy, Mahe 7, Kitaro, Liberty, Shinano Red, Koutoku |

5) Measurement Results with Color/Color Difference Meter

The results of measurement for comparison of browning degree in grated apples (No. 1) with a color/color difference meter are shown in Table 5. In values of L*, a*, and b*, the a* value related to red color change was low for "Aori No. 27", compared to other cultivars. In addition, change in the Δa* value was the lowest of all for "Aori No. 27". Accordingly, it was confirmed that red color change is low for "Aori No. 27". In addition, a color/color difference meter revealed that the ΔE value was the lowest of all for Aori No. 27, and there was less color change during the period of immediately after grating to 1 day after grating.

3) Measurement Results with Color/Color Difference Meter

Each of tables 6, 7, 8, 9, 10 and 11 shows the results of measurement with a color/color difference meter for the comparison of browning degree in grated apples (No. 2). The tables show change over time up to 24 hours in the values of L*, a*, b*, E* and ΔE as well as hue, respectively. Further, FIGS. 2-1, 2-2, 2-3, 2-4, 2-5 and 2-6 are graphs showing the results of measurement in the respective tables, which indicate change over time up to 24 hours in the values of L*, a*, b*, E*, ΔE* as well as hue, respectively.

The a* value corresponds accurately to red color change. During the period of immediately after grating to 24 hours

TABLE 5

Values of color difference meter for browning degree of grated fruits

| No. | Name of cultivars | Immediately after grating | | | 1 day after | | | Difference between immediately after grating and 1 day after | | | |
|---|---|---|---|---|---|---|---|---|---|---|---|
| | | L* value | a* value | b* value | L* value | a* value | b* value | ΔL* value | Δa* value | Δb* value | ΔE |
| 1 | Aori No. 27 | 68.8 | −2.63 | 25.5 | 57.2 | −2.52 | 20.7 | 11.6 | 0.11 | 4.78 | 12.6 |
| 2 | Seimei | 67.9 | −3.38 | 18.2 | 49.8 | 1.92 | 18.3 | 18.1 | 5.30 | −0.13 | 18.9 |
| 3 | Elstar | 69.0 | −3.52 | 25.0 | 51.1 | 0.90 | 17.2 | 17.9 | 4.42 | 7.82 | 20.1 |
| 4 | Jonagold | 66.2 | −4.19 | 23.4 | 48.3 | 4.92 | 20.0 | 17.9 | 9.10 | 3.47 | 20.4 |
| 5 | Hida | 74.1 | −3.57 | 23.5 | 53.2 | 1.25 | 23.0 | 20.9 | 4.82 | 0.50 | 21.4 |
| 6 | Shinano Gold | 72.2 | −3.92 | 24.4 | 50.8 | 0.91 | 19.4 | 21.3 | 4.83 | 5.03 | 22.5 |
| 7 | Senshu | 70.1 | −3.09 | 18.1 | 47.9 | 3.76 | 17.0 | 22.2 | 6.85 | 1.02 | 23.2 |
| 8 | Shinano Sweet | 68.1 | −0.32 | 21.1 | 45.4 | 7.23 | 20.1 | 22.7 | 7.55 | 1.00 | 24.0 |
| 9 | Mahe 7 | 68.1 | −3.87 | 18.8 | 45.4 | 3.24 | 14.1 | 22.7 | 7.11 | 4.67 | 24.3 |
| 10 | Akita gold | 74.0 | −4.50 | 25.9 | 51.0 | 3.29 | 25.5 | 23.0 | 7.79 | 0.42 | 24.3 |
| 11 | Kitaro | 72.8 | −4.15 | 19.9 | 49.7 | 4.44 | 20.6 | 23.2 | 8.59 | −0.76 | 24.7 |
| 12 | Ourin | 69.7 | −0.97 | 21.6 | 45.9 | 8.69 | 22.0 | 23.7 | 9.66 | −0.33 | 25.6 |
| 13 | Starking Delicious | 69.6 | −0.61 | 21.2 | 45.5 | 8.21 | 23.1 | 24.1 | 8.82 | −1.88 | 25.7 |
| 14 | Hoshi-no-Kinka | 68.9 | −1.91 | 23.2 | 44.6 | 7.61 | 20.8 | 24.3 | 9.52 | 2.41 | 26.2 |
| 15 | Indo | 74.6 | −2.12 | 19.9 | 49.2 | 6.16 | 22.7 | 25.3 | 8.27 | −2.88 | 26.8 |
| 16 | Mutsu | 72.6 | −4.29 | 25.2 | 47.4 | 5.17 | 20.9 | 25.3 | 9.46 | 4.32 | 27.3 |
| 17 | Mellow | 70.8 | −4.22 | 24.1 | 45.3 | 5.32 | 18.2 | 25.5 | 9.54 | 5.90 | 27.9 |
| 18 | Kinsei | 71.6 | −3.20 | 21.7 | 44.8 | 6.01 | 18.3 | 26.9 | 9.22 | 3.40 | 28.6 |
| 19 | Ambitious | 77.4 | −4.94 | 21.1 | 50.3 | 4.93 | 21.9 | 27.1 | 9.87 | −0.81 | 28.8 |
| 20 | Fuji | 75.4 | −4.74 | 26.7 | 46.9 | 4.92 | 21.3 | 28.5 | 9.66 | 5.39 | 30.6 |
| 21 | Asahi | 72.6 | −4.48 | 15.7 | 45.0 | 8.73 | 19.8 | 27.6 | 13.20 | −4.04 | 30.9 |
| 22 | Toko | 71.5 | −4.02 | 19.8 | 41.9 | 5.16 | 16.0 | 29.6 | 9.18 | 3.83 | 31.2 |
| 23 | Golden Delicious | 70.4 | −3.86 | 26.2 | 41.3 | 6.11 | 17.5 | 29.1 | 9.96 | 8.72 | 31.9 |

$\Delta E = \sqrt{(\Delta L^*)^2 + (\Delta a^*)^2 + (\Delta b^*)^2}$

7. Comparison of Browning Degree in Grated Apples (No. 2) Change Over Time Up to 24 Hours Later.

1) Cultivars Under Test

The following 5 cultivars were under test, including "Aori No. 27" of the present invention; "Elstar", "Seimei" and "Mellow" in which browning is relatively less likely to occur; and "Fuji" in which browning is most likely to occur.

2) Method for Investigation and Measurement

A well-ripened fruit of each cultivar under test was used. After removing the skin and grating the flesh, the flesh was put on a Petri dish to measure color change over time (15 minutes after grating, 30 minutes after, 1, 2, 3, 4 and 5 hours after, 10 hours after, 15 hours after, and 24 hours after) with a color/color difference meter and investigate the browning degree based on the browning index. Both measurement and investigation were conducted in the same manner as in the case of <6>.

later, the a* value was increased for all cultivars except "Aori No. 27" in which there was almost no change (Table 7, FIG. 2-2). As described in the following findings of browning index, this corresponds accurately to the results that the flesh color of "Aori No. 27" hardly turns brown in visual observation.

Further, change in hue was small for "Aori No. 27", compared to other cultivars (Table 11, FIG. 2-6).

Figures 1, 2:
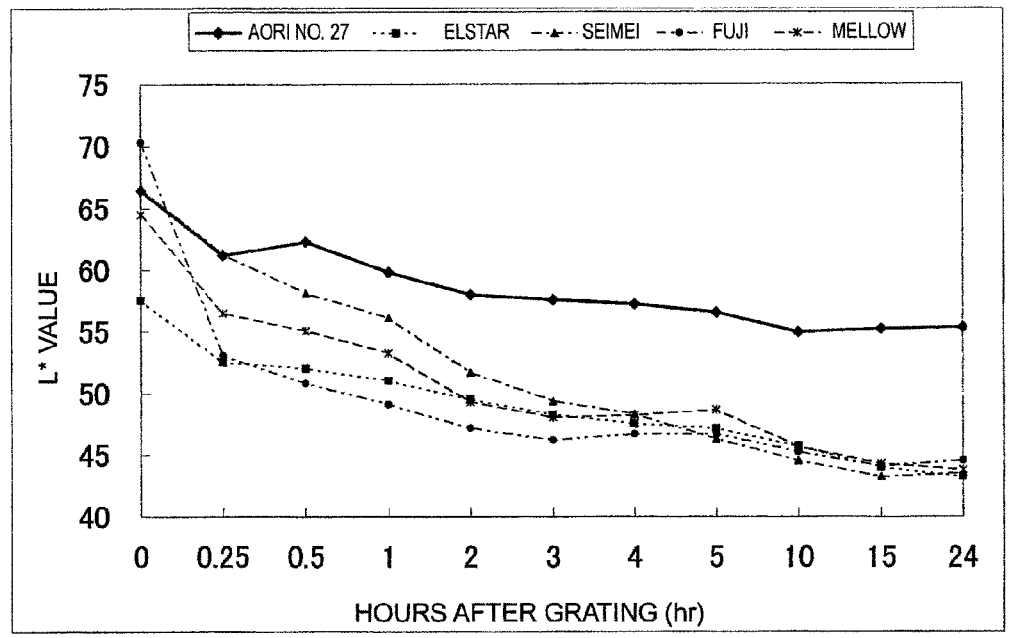
Figure 2:
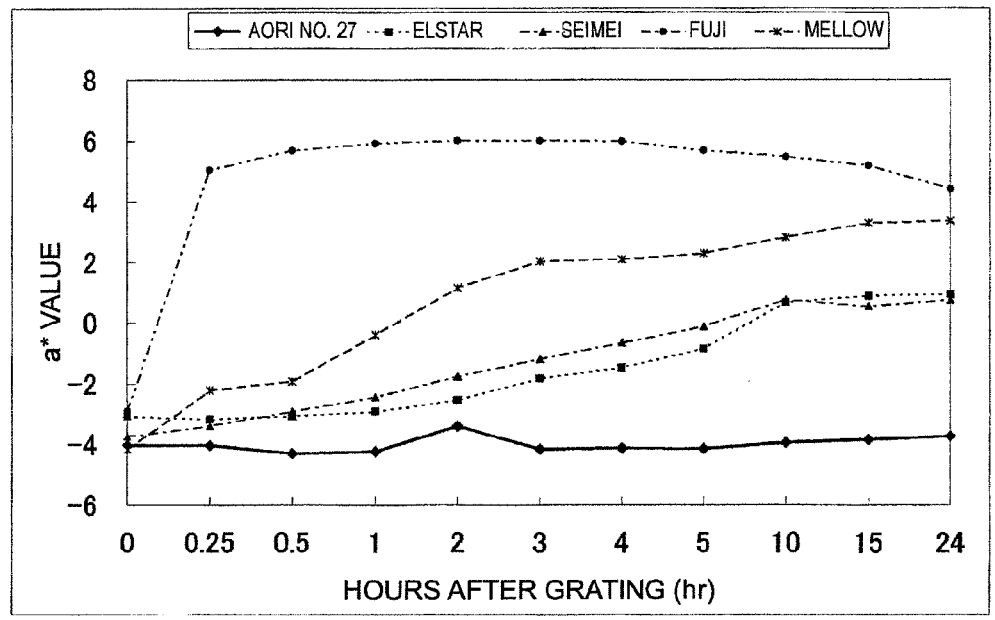

The reduction in the L* value of "Aori No. 27" was smaller than other cultivars during the period of immediately after grating to 24 hours ater, which demonstrates that the drop of brightness is small (Table 6, FIG. 2-1). The similar tendency was seen in the E* value (Table 9, FIG. 2-4).

The ΔE values of "Aori No. 27" and "Elstar" changed at about the same level, but that of "Aori No. 27" was likely to be lower than that of "Elstar" on and 15 hours after (Table 10, FIG. 2-5).

TABLE 6

L* value

| Time | | Aori No. 27 | Elstar | Seimei | Fuji | Mellow |
|---|---|---|---|---|---|---|
| Immediately after grating | 0 | 66.5 | 57.5 | 66.7 | 70.3 | 64.5 |
| 15 minutes after | 0.25 | 61.2 | 52.5 | 61.3 | 53.1 | 56.5 |
| 30 minutes after | 0.5 | 62.3 | 52.0 | 58.1 | 50.8 | 55.0 |
| 1 hour after | 1 | 59.8 | 51.0 | 56.1 | 49.1 | 53.3 |
| 2 hours after | 2 | 58.0 | 49.5 | 51.7 | 47.2 | 49.3 |
| 3 hours after | 3 | 57.6 | 48.3 | 49.4 | 46.2 | 48.1 |
| 4 hours after | 4 | 57.2 | 47.5 | 48.3 | 46.7 | 48.2 |
| 5 hours after | 5 | 56.5 | 47.2 | 46.3 | 46.7 | 48.7 |
| 10 hours after | 10 | 54.9 | 45.7 | 44.5 | 45.2 | 45.6 |
| 15 hours after | 15 | 55.2 | 44.0 | 43.3 | 44.1 | 44.3 |
| 24 hours after | 24 | 55.3 | 43.3 | 43.6 | 44.6 | 43.8 |

TABLE 7 a* value

| Time | | Aori No. 27 | Elstar | Seimei | Fuji | Mellow |
|---|---|---|---|---|---|---|
| Immediately after grating | 0 | −4.02 | −3.07 | −3.74 | −2.88 | −4.18 |
| 15 minutes after | 0.25 | −4.03 | −3.16 | −3.39 | 5.04 | −2.22 |
| 30 minutes after | 0.5 | −4.31 | −3.07 | −2.91 | 5.68 | −1.92 |
| 1 hour after | 1 | −4.24 | −2.92 | −2.44 | 5.92 | −0.40 |
| 2 hours after | 2 | −3.40 | −2.54 | −1.76 | 6.00 | 1.15 |
| 3 hours after | 3 | −4.17 | −1.83 | −1.19 | 6.00 | 2.03 |
| 4 hours after | 4 | −4.13 | −1.48 | −0.67 | 5.98 | 2.09 |
| 5 hours after | 5 | −4.15 | −0.85 | −0.13 | 5.69 | 2.28 |
| 10 hours after | 10 | −3.94 | 0.66 | 0.75 | 5.47 | 2.82 |
| 15 hours after | 15 | −3.85 | 0.88 | 0.53 | 5.18 | 3.27 |
| 24 hours after | 24 | −3.74 | 0.92 | 0.73 | 4.41 | 3.36 |

TABLE 8 b* value

| Time | | Aori No. 27 | Elstar | Seimei | Fuji | Mellow |
|---|---|---|---|---|---|---|
| Immediately after grating | 0 | 22.9 | 16.5 | 17.9 | 23.0 | 23.3 |
| 15 minutes after | 0.25 | 22.0 | 13.1 | 16.3 | 22.0 | 20.2 |
| 30 minutes after | 0.5 | 22.8 | 12.6 | 15.7 | 21.1 | 20.3 |
| 1 hour after | 1 | 21.6 | 12.5 | 16.0 | 20.9 | 21.2 |
| 2 hours after | 2 | 20.5 | 11.9 | 15.2 | 20.8 | 20.2 |
| 3 hours after | 3 | 21.0 | 11.4 | 15.1 | 20.8 | 20.2 |
| 4 hours after | 4 | 20.6 | 12.3 | 16.3 | 21.1 | 18.1 |
| 5 hours after | 5 | 20.6 | 12.5 | 16.6 | 20.9 | 21.8 |
| 10 hours after | 10 | 19.0 | 13.5 | 16.8 | 19.8 | 20.3 |
| 15 hours after | 15 | 18.6 | 13.8 | 16.1 | 20.6 | 19.5 |
| 24 hours after | 24 | 18.6 | 14.0 | 16.2 | 20.4 | 20.1 |

TABLE 9

E* value

| Time | | Aori No. 27 | Elstar | Seimei | Fuji | Mellow |
|---|---|---|---|---|---|---|
| Immediately after grating | 0 | 70.4 | 59.9 | 69.1 | 74.0 | 68.7 |
| 15 minutes after | 0.25 | 65.2 | 54.2 | 63.5 | 57.7 | 60.0 |
| 30 minutes after | 0.5 | 66.5 | 53.6 | 60.3 | 55.3 | 59.3 |
| 1 hour after | 1 | 63.7 | 52.6 | 58.4 | 53.7 | 57.3 |
| 2 hours after | 2 | 61.6 | 51.0 | 53.9 | 51.9 | 53.3 |
| 3 hours after | 3 | 61.4 | 49.6 | 51.6 | 51.0 | 52.2 |
| 4 hours after | 4 | 60.9 | 49.1 | 51.0 | 51.6 | 51.6 |
| 5 hours after | 5 | 60.3 | 48.8 | 49.2 | 51.5 | 53.4 |
| 10 hours after | 10 | 58.2 | 47.6 | 47.6 | 49.7 | 50.0 |
| 15 hours after | 15 | 58.3 | 46.1 | 46.2 | 48.9 | 48.5 |
| 24 hours after | 24 | 58.4 | 45.5 | 46.5 | 49.2 | 48.3 |

TABLE 10

ΔE value

| Time | | Aori No. 27 | Elstar | Seimei | Fuji | Mellow |
|---|---|---|---|---|---|---|
| 15 minutes after | 0.25 | 5.7 | 6.1 | 5.6 | 19.0 | 8.8 |
| 30 minutes after | 0.5 | 4.2 | 6.8 | 8.9 | 21.4 | 10.2 |
| 1 hour after | 1 | 6.8 | 7.7 | 10.8 | 23.0 | 12.1 |
| 2 hours after | 2 | 8.9 | 9.3 | 15.3 | 24.9 | 16.4 |
| 3 hours after | 3 | 9.1 | 10.7 | 17.7 | 25.8 | 17.9 |
| 4 hours after | 4 | 9.5 | 11.0 | 18.7 | 25.3 | 18.2 |
| 5 hours after | 5 | 10.2 | 11.4 | 20.7 | 25.2 | 17.2 |
| 10 hours after | 10 | 12.2 | 12.8 | 22.6 | 26.6 | 20.4 |
| 15 hours after | 15 | 12.1 | 14.4 | 23.9 | 27.6 | 21.9 |
| 1 day after | 24 | 12.0 | 15.0 | 23.6 | 26.9 | 22.3 |

TABLE 11

Hue (angle: θ, tanθ = b*/a*)

| Time | | Aori No. 27 | Elstar | Seimei | Fuji | Mellow |
|---|---|---|---|---|---|---|
| Immediately after grating | 0 | 100 | 101 | 102 | 97 | 100 |
| 15 minutes after | 0.25 | 100 | 104 | 102 | 77 | 96 |
| 30 minutes after | 0.5 | 101 | 104 | 100 | 75 | 95 |
| 1 hour after | 1 | 101 | 103 | 99 | 74 | 91 |
| 2 hours after | 2 | 99 | 102 | 97 | 74 | 87 |
| 3 hours after | 3 | 101 | 99 | 95 | 74 | 84 |
| 4 hours after | 4 | 101 | 97 | 92 | 74 | 83 |
| 5 hours after | 5 | 101 | 94 | 90 | 75 | 84 |
| 10 hours after | 10 | 102 | 87 | 87 | 75 | 82 |
| 15 hours after | 15 | 102 | 86 | 88 | 76 | 80 |
| 24 hours after | 24 | 101 | 86 | 87 | 78 | 80 |

4) Change in Browning Index

Table 12 shows change over time up to 24 hours in the browning index for the comparison of browning degree in grated apples (No. 2). As shown in the table, in 24 hours after grating, there was almost no change in the flesh color of "Aori No. 27", but the yellow color became somewhat darker, which suggests that "Aori No. 27" was virtually "unbrowning". Meanwhile, "Elstar", in which the browning degree was relatively low and there was not so much difference in the above-described measurement with a color/color difference meter, partially started browning 1 hour after grating and already reached the level of the browning index 2 at 5 hours after. Further, browning of "Seimei" started 30 minutes after grating, and it reached the browning index 2 at 2 hours after. Browning of "Mellow" started 15 minutes after grating, and it reached the browning index 3 at 10 hours after. Browning of "Fuji" started immediately after grating, and it reached the browning index 5 at 1 hour after grating.

Accordingly, browning of the conventional cultivars starts within 24 hours after grating, and more specifically, it starts at quite early stage, and the browning degree was saturated quickly. However, it has been revealed that a non-browning apple "Aori No. 27" of the present invention does not turn brown at all during that period.

TABLE 12

| Time | Name of cultivars | | | | |
|---|---|---|---|---|---|
| | Aori No. 27 | Elstar | Seimei | Mellow | Fuji |
| Immediately after grating | 0(2504) | 0(2504) | 0(2504) | 0(2503) | 0(2504) |
| 15 minutes after | 0(2504) | 0 | 0 | 1 | 3 |
| 30 minutes after | 0(2504) | 0 | 1 | 2 | 4 |
| 1 hour after | 0(2504) | 1 | 1 | 2 | 5 |
| 2 hours after | 0(2505) | 1 | 2 | 2 | 5 |
| 3 hours after | 0(2505) | 1 | 2 | 2 | 5 |
| 4 hours after | 0(2505) | 1 | 2 | 2 | 5 |
| 5 hours after | 0(2505) | 2 | 2 | 2 | 5 |
| 10 hours after | 0(2505) | 2 | 2 | 3 | 5 |
| 15 hours after | 0(2505) | 2 | 2 | 3 | 5 |
| 24 hours after | 0(2506) | 2 | 2 | 3 | 5 |

8. Comparison of Browning Degree in Grated Apples (No. 3) Change Over Time Up to 5 Days Later.

1) Cultivars Under Test

The following 4 cultivars were under test, including "Aori No. 27"; "Seimei" and "Mellow" in which browning is relatively less likely to occur; and "Fuji" in which browning is most likely to occur.

2) Method of Investigation and Measurement

A well-ripened fruit of each cultivar under test was used. After removing the skin and grating the flesh, the flesh was put on a Petri dish to investigate color change and browning degree over time (1 day after grating, 3 days after and 5 days after) with a color/color difference meter. The measurement with a color/color difference meter was performed in the same manner as in the case of <7>.

3) Change of Browning Degree in 1 to 5 Days

Each of Tables 13, 14, 15, 16 and 17 shows the results of measurement with a color/color difference meter for the comparison of browning degree in grated apples (No. 3). The tables show change in the values of L*, a*, b* and ΔE as well as hue over time up to 5 days later, respectively. In Table 16, a color chart is shown as well. Further, FIGS. 3-1, 3-2, 3-3, 3-4 and 3-5 are graphs of the results of measurement in the respective tables, which show change over time up to 5 days later in the values of L*, a*, b* and ΔE as well as hue. It is to be noted that FIG. 3P is a photograph showing the comparison of browning degree in grated apples after three days in which "Aori No. 27" of the present invention and "Fuji" were compared. In the figure, "Aori No. 27" and "Fuji" are shown on the left and right sides, respectively.

Change in the a* value of "Aori No. 27" was small over 5 days after grating. Such values of other cultivars changed largely from negative to positive, suggesting increase in the red color of fleshes (Table 14, FIG. 3-2). Further, change in hue of "Aori No. 27 was small, compared to other cultivars (Table 17, FIG. 3-5).

Figures 2, 3:
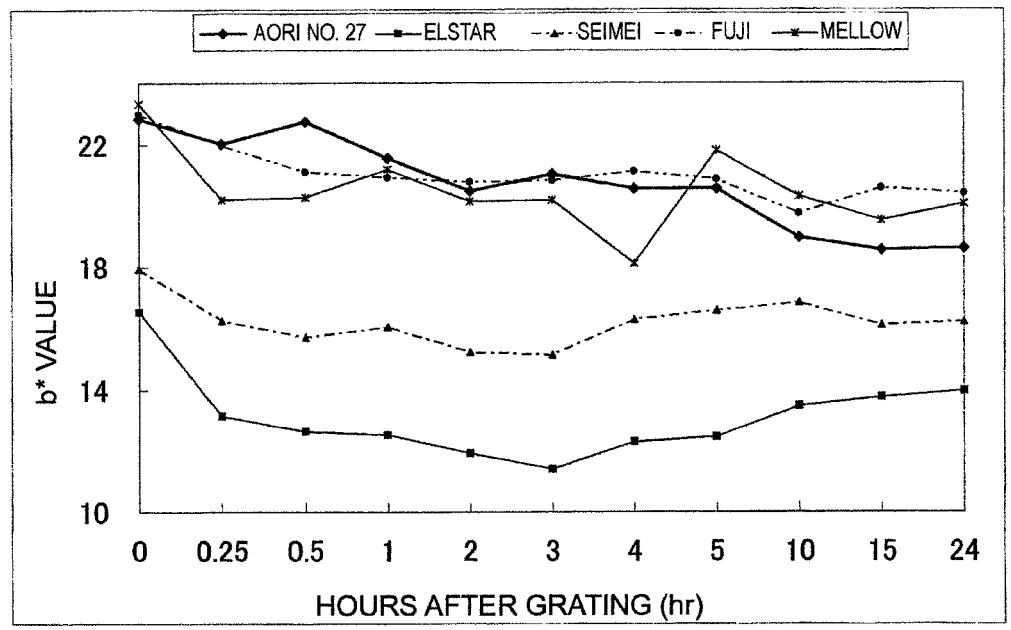
Figures 1, 3:
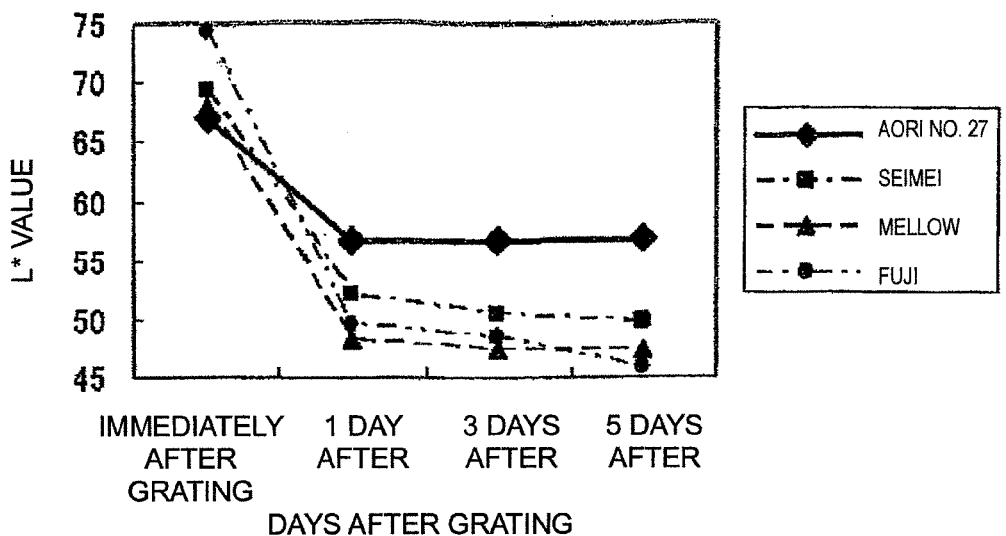
Figures 2, 3:
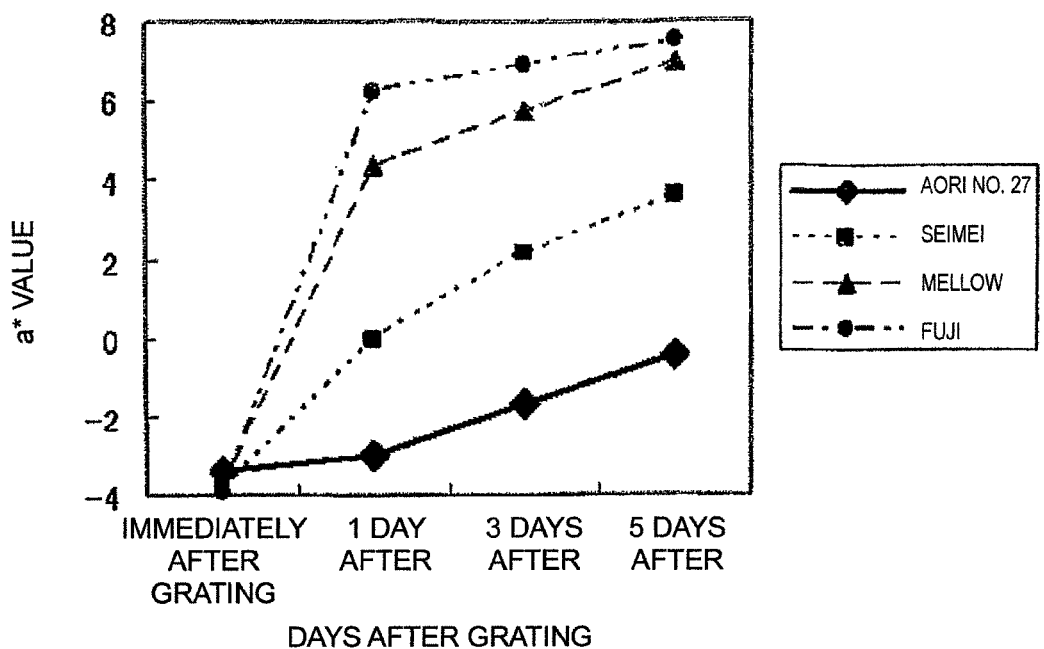
Figure 3:
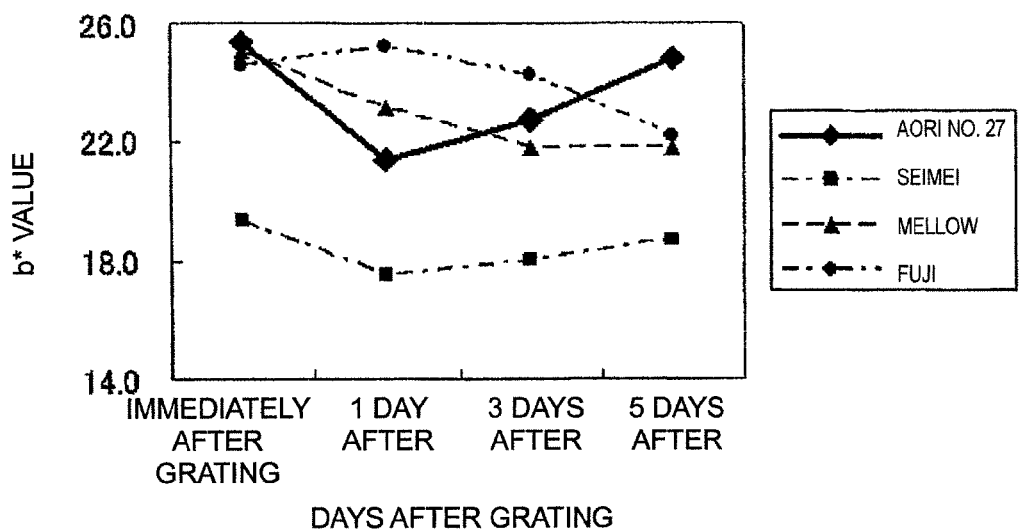
Figures 3, 4:
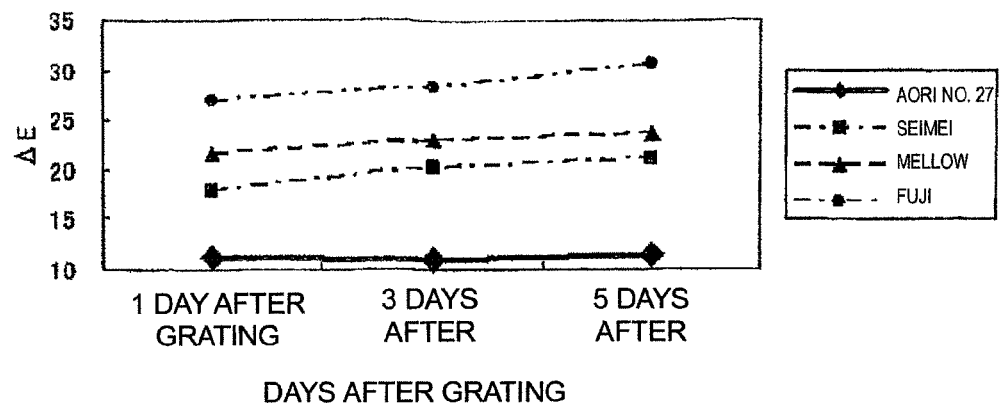
Figures 3, 4, 5:
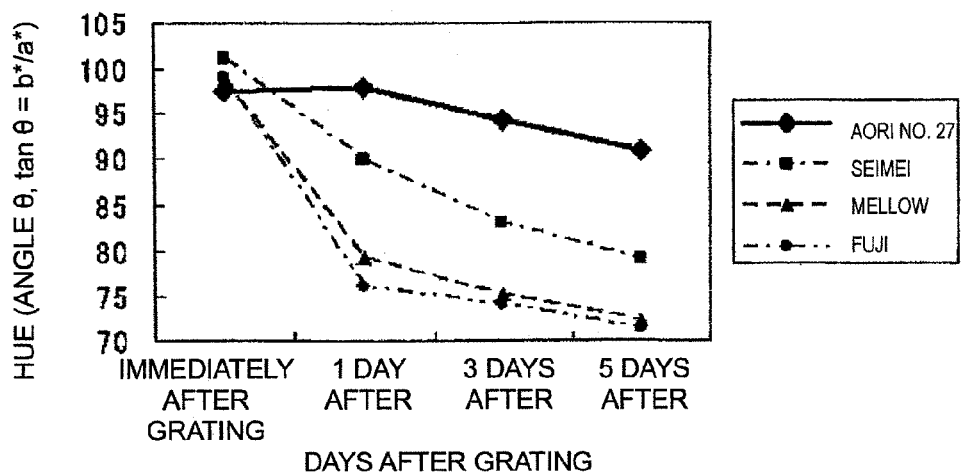
Figure 3P:
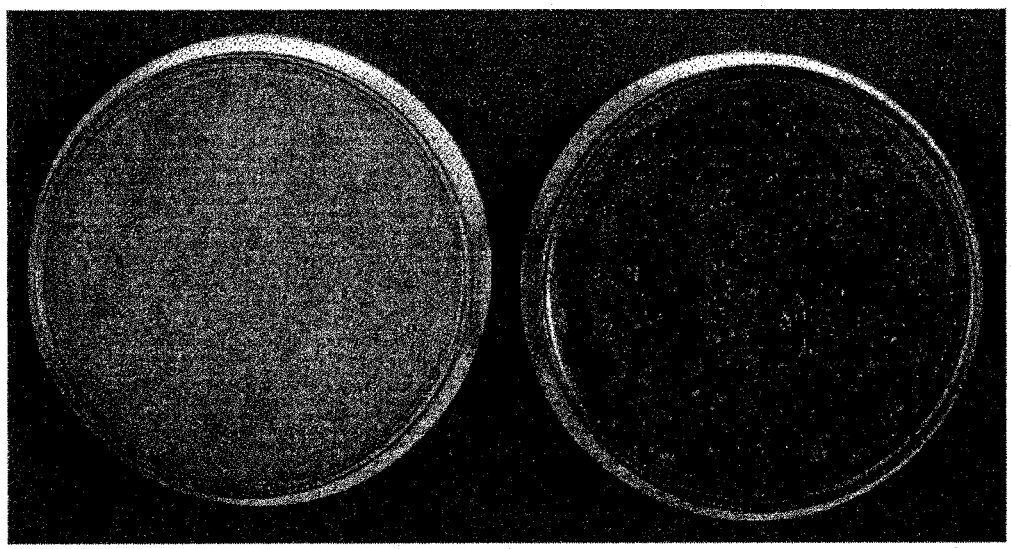
FIG. 3P is a photograph comparing the browning degrees of grated apples 3 days after grating, wherein "Aori No. 27" of the present invention and "Fuji" were compared.

In addition, the L* value of "Aori No. "27" was higher since 1 day after grating, and brightness was maintained at the higher level (Table 13, FIG. 3-1).

Figures 2, 3, 4:
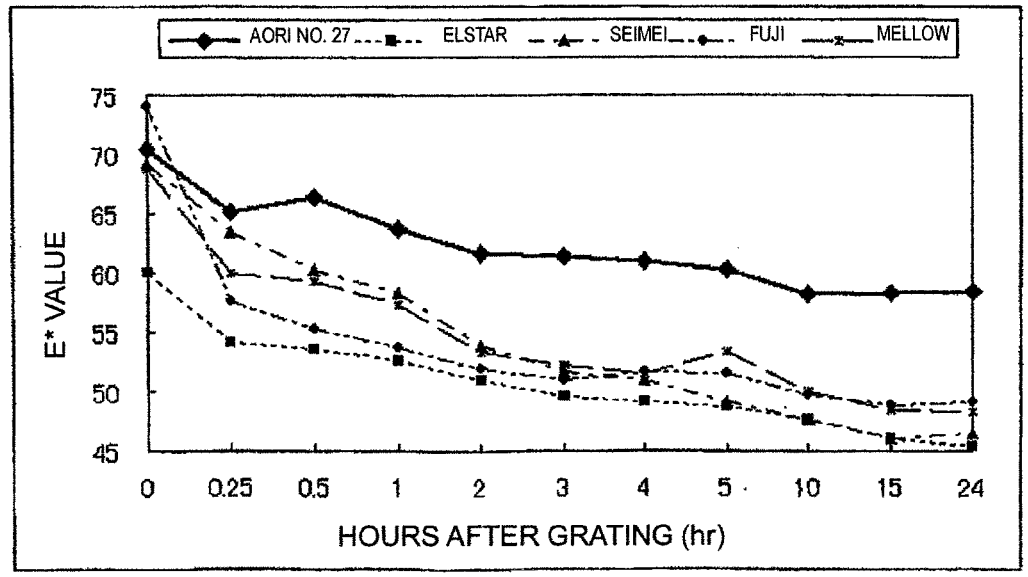

The ΔE value of "Aori No. 27" was lower than that of other cultivars in addition to small color change (Table 16, FIG. 3-4).

According to the color chart based on the Japan Color Standard for Horticultural Plants, the color of "Aori No. 27" in 5 days after grating corresponded to 2203 (bright reddish yellow), and color change thereof was apparently small compared to other cultivars (Table 16).

As described above, it has been revealed that, in the non-browning apple "Aori No. 27" of the present invention, browning of flesh does not virtually occur or is suppressed significantly even in 5 days after grating.

TABLE 13

| | L* value | | | |
|---|---|---|---|---|
| Name of cultivars | Immediately after grating | 1 day after | 3 days after | 5 days after |
| Aori No. 27 | 67.0 | 56.6 | 56.6 | 56.9 |
| Seimei | 69.5 | 52.1 | 50.4 | 49.8 |
| Mellow | 68.0 | 48.2 | 47.3 | 47.3 |
| Fuji | 74.4 | 49.6 | 48.4 | 45.9 |

TABLE 14

| | a* value | | | |
|---|---|---|---|---|
| Name of cultivars | Immediately after grating | 1 day after | 3 days after | 5 days after |
| Aori No. 27 | −3.40 | −3.00 | −1.70 | −0.44 |
| Seimei | −3.84 | −0.04 | 2.16 | 3.63 |
| Mellow | −3.78 | 4.39 | 5.72 | 6.98 |
| Fuji | −3.93 | 6.21 | 0.92 | 7.50 |

TABLE 15

| | b* value | | | |
|---|---|---|---|---|
| Name of cultivars | Immediately after grating | 1 day after | 3 days after | 5 days after |
| Aori No. 27 | 25.3 | 21.4 | 22.7 | 24.8 |
| Seimei | 19.3 | 17.5 | 18.0 | 18.7 |
| Mellow | 25.1 | 23.1 | 21.8 | 21.8 |
| Fuji | 24.6 | 25.2 | 24.2 | 22.2 |

TABLE 16

| | ΔE | | | |
|---|---|---|---|---|
| Name of cultivars | 1 day after grating | 3 days after | 5 days after | Color chart 5 days after grating (color chart based on the Japan Color Standard for Horticultural Plants) |
| Aori No. 27 | 11.2 | 11.0 | 11.5 | 2203 (Bright reddish yellow) |
| Seimei | 17.9 | 20.1 | 21.1 | 1914 (Light yellowish brown) |
| Mellow | 21.5 | 23.0 | 23.6 | 1612 (Light brown) |
| Fuji | 26.8 | 28.2 | 30.7 | 1608 (Bister) |

TABLE 17

| Name of cultivars | Hue (angle; θ, tanθ = b*/a*) | | | |
|---|---|---|---|---|
| | Immediately after grating | 1 day after | 3 days after | 5 days after |
| Aori No. 27 | 98 | 98 | 94 | 91 |
| Seimei | 101 | 90 | 83 | 79 |
| Mellow | 99 | 79 | 75 | 72 |
| Fuji | 99 | 76 | 74 | 71 |

9. Comparison of Browning Degree of Apples After Thawing.

"Aori No. 27" of the present invention and the conventional apples were compared and investigated for changes in apple flesh colors after freezing and thawing.

1) Cultivars Under Test

"Aori No. 27", "Seimei", "Mellow" and "Fuji" were under test.

2) Method of Investigation

Fruits of cultivars under test were put in a freezer (−15° C.) one by one. They were left for 24 hours and then thawed at room temperature (10 to 25° C.). The fruits were cut in cross section in 5 hours and 1 day after taking out of the freezer to investigate browning degree based on the browning index. In addition, the surface of the flesh was clothed in Saran Wrap on which a measurement head of a color/color difference meter was put for measurement. It is to be noted that the investigation of the browning index and the measurement with the color/color difference meter were conducted in the same manner as in the case of each test described above.

4) Results of Investigation and Measurement

Figures 2, 4:
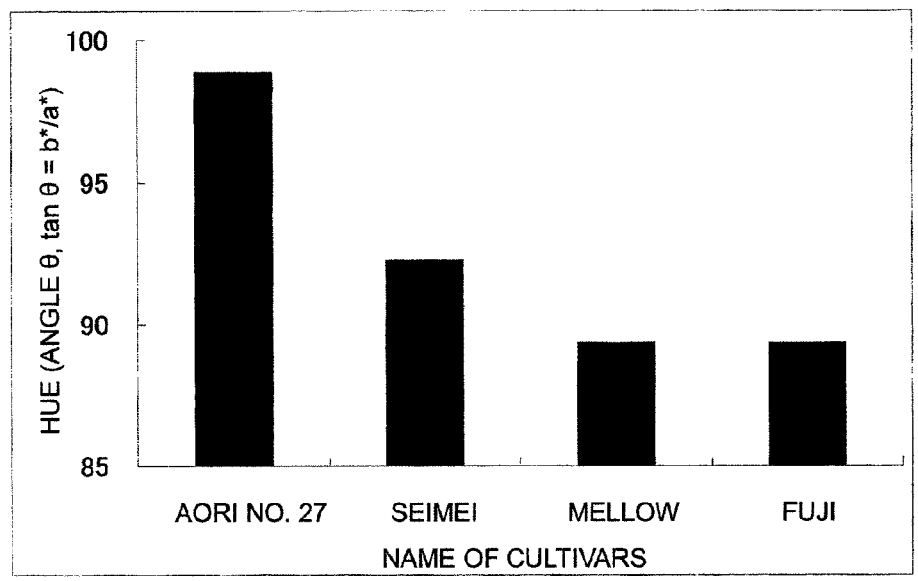
Figure 4P:
FIG. 4P is a photograph comparing the browning degrees of cut surfaces of frozen apples 1 day after taking out of a freezer, wherein "Aori No. 27" of the present invention and "Fuji" were compared.

The results of investigation for the browning indexes of apples after taking out of a freezer are shown in Table 18. In addition, the results of measurement for values of a color/color difference meter such as L*, a* and b* are shown in Table 19 and hue in Table 20. Further, FIG. 4-1 is a graph showing the results of measurement for a* values of apples in 1 day after taking out of a freezer, and FIG. 4-2 is a graph showing hue in 1 day after taking out of a freezer. It is to be noted that FIG. 4P is a photograph comparing the browning degrees of cut surfaces of frozen apples in 1 day after taking out of a freezer, wherein "Aori No. 27" of the present invention and "Fuji" were compared. In the figure, "Aori No. 27" and "Fuji" are shown on the left and right sides, respectively.

At the time of cutting in 5 hours after taking out of a freezer, fleshes of any cultivars under test took on the yellow color, wherein the browning index was 0. However, at the time of cutting 1 day after grating, browning was observed in "Seimei", "Mellow" and "Fuji". Meanwhile, browning was not observed in "Aori No. 27" at all, but the yellow color became somewhat darker compared to that in 5 hours after taking out of a freezer, which suggests that "Aori No. 27" was virtually "non-browning" (Table 18).

TABLE 18

| | Browning index | |
|---|---|---|
| Name of cultivars | 5 hours after taking out of a freezer | 1 day after taking out of a freezer |
| Aori No. 27 | 0 (2504) | 0 (2505) |
| Seimei | 0 (2504) | 2 (1914) |
| Mellow | 0 (2505) | 3 (1914) |
| Fuji | 0 (2503) | 5 (1613) |

Values in parentheses is in accordance with the color chart based on the Japan Color Standard for Horticultural Plants.

In the values of a color/color difference meter, the a* value, which changes significantly due to browning, was not more than −2 for all cultivars in 5 days after taking out of a freezer. However, in 1 day after taking out of a freezer, the a* value increased to positive for "Seimei", "Mellow" and "Fuji". Meanwhile, it was found only in "Aori No. 27" that the a* value changed from about −2.31 to −3.37, and no increase in red color was observed (Table 19, FIG. 4-1).

It was also revealed that hue in 1 day after taking out of a freezer was higher for "Aori No. 27" than other cultivars in addition to small color change (Table 20, FIG. 4-2).

As described above, it has been revealed that, in a non-browning apple "Aori No. 27" of the present invention, browning of flesh does not virtually occur even after freezing and thawing.

TABLE 19

| Name of cultivars | 5 hours after taking out of a freezer | | | 1 day after taking out of a freezer | | | Difference during the period of 5 hours after taking out of a freezer and 1 day after taking out of a freezer | | |
|---|---|---|---|---|---|---|---|---|---|
| | L* value | a* value | b* value | L* value | a* value | b* value | ΔL* value | Δa* value | Δb* value |
| Aori No. 27 | 65.5 | −2.31 | 17.3 | 62.7 | −3.37 | 21.6 | −2.8 | −1.1 | 4.3 |
| Seimei | 64.9 | −2.07 | 14.2 | 60.9 | −0.66 | 16.8 | −4.0 | 1.4 | 2.6 |
| Mellow | 69.0 | −3.07 | 19.8 | 60.5 | 2.19 | 21.7 | −8.5 | 5.3 | 1.9 |
| Fuji | 66.2 | −2.04 | 17.3 | 60.3 | 2.89 | 22.0 | −5.9 | 4.9 | 4.6 |

TABLE 20

Hue in 1 day after taking out of a freezer (Angle θ, tanθ = b*/a*)

| Name of cultivars | 1 day after grating |
|---|---|
| Aori No. 27 | 99 |
| Seimei | 92 |
| Mellow | 89 |
| Fuji | 89 |

INDUSTRIAL APPLICABILITY

Some apple applications which may be newly developed by a non-browning apple of the present invention will now be described. Firstly, it is possible to newly provide apples to be eaten raw for restaurants, school and hospital meals or other food industries, including cut apples; peeled apples prepared by removing the skin in advance for easy to eat; or vacuum-packed or frozen product thereof. Further, grated apples can expand its application as an easy-to-eat food for inpatients infants or elderly. In view of "unbrowning" even in the processing step, the availability of the inventive apples can be expanded to juice and other drinks, jellies, or confectioneries, wherein the needs of additives are eliminated. Since flesh can be refrigerated without browning after thawing, the use thereof can be expanded newly to processed foods that require freezing and thawing.

In any of these applications, the use of the present invention makes it possible to provide virtually "unbrowning" in apple, and in consequence, appearance may be improved significantly without using any conventional additives to prevent discoloration, which allows adding great marketability and also increasing consumption of apples in an effective manner. Therefore, the industrial applicability of the present invention is very high in each of the first, second and third industrial fields, which involve in food.

A deposit was made of seeds of non-browning apple designated "Aori No. 27" with the International Patent Organization Depository, AIST Tsukuba Central 6 1-1, Higashi 1-chome Tsukuba-shi, Ibaraki-ken 305-8566 Japan. The deposit was assigned accession number FERM BP-11456. The date of the deposit was Jan. 18, 2012. The deposit was made in accordance with Budapest Treaty requirements and 37 C.F.R. §1.801-1.809, and all restrictions regarding availability to the public will be irrevocably removed without restriction upon granting of the patent.

The invention claimed is:

1. A non-browning apple designated as "Aori No. 27", wherein a representative sample of seed of said apple was deposited under international deposit number FERM BP-11456, which under visual evaluation has a non-browning characteristic of (A) a characteristic that after grated apple flesh prepared by removing the skin and grating the flesh is left at 10 to 25° C. for up to 5 days, the grated apple flesh does not turn brown; and (B) a characteristic that after a fruit is frozen and thawed, flesh thereof does not turn brown for up to 1 day after thawing and wherein said apple is mutually cross compatible with cultivars "Fuji", "Tsugaru" and "Ourin"; and being compatible as a pollenizer for cultivar "Jonagold".

2. A non-browning apple designated as "Aori No. 27", wherein a representative sample of seed of said apple was deposited under international deposit number FERM BP-11456, which under visual evaluation has a non-browning characteristic of (A) a characteristic that after grated apple flesh prepared by removing the skin and grating the flesh is left at 10 to 25° C. for up to 5 days, the grated apple flesh does not turn brown; and (B) a characteristic that after a fruit is frozen and thawed, flesh thereof does not turn brown for up to 1 day after thawing and wherein said apple has a maturity of about 1 day earlier than "Ourin"; a tree altitude of intermediate and a tree size and vigor of both medium; a flow-bud formation and spur bearing; and resistance to *Alternaria* blotch.

* * * * *